(12) United States Patent
Sato

(10) Patent No.: US 11,313,850 B2
(45) Date of Patent: Apr. 26, 2022

(54) SMALL PARTICLE MEASUREMENT SYSTEM

(71) Applicant: ADVANTEST CORPORATION, Tokyo (JP)

(72) Inventor: Hiroshi Sato, Tokyo (JP)

(73) Assignee: ADVANTEST CORPORATION, Tokyo (JP)

( * ) Notice: Subject to any disclaimer, the term of this patent is extended or adjusted under 35 U.S.C. 154(b) by 256 days.

(21) Appl. No.: 16/548,096

(22) Filed: Aug. 22, 2019

(65) Prior Publication Data

US 2020/0072815 A1 Mar. 5, 2020

(30) Foreign Application Priority Data

Sep. 4, 2018 (JP) .............................. JP2018-165314

(51) Int. Cl.
*G01N 33/487* (2006.01)
*G01N 27/447* (2006.01)

(52) U.S. Cl.
CPC . *G01N 33/48721* (2013.01); *G01N 27/44791* (2013.01)

(58) Field of Classification Search
CPC .......... G01N 27/447–44795; G01N 33/48721; G01N 33/48728
USPC ................ 204/450–470, 546–550, 600–621, 204/643–645
See application file for complete search history.

(56) References Cited

U.S. PATENT DOCUMENTS

| 9,395,729 | B1 | 7/2016 | Yang et al. |
| 9,995,729 | B2 * | 6/2018 | Nakamura ....... G01N 33/48728 |
| 2009/0136958 | A1 * | 5/2009 | Gershow .............. C12Q 1/6869 |
| | | | 435/6.13 |
| 2016/0154032 | A1 * | 6/2016 | Kuramochi ......... H03F 3/45475 |
| | | | 324/120 |

FOREIGN PATENT DOCUMENTS

| JP | 2001305041 A | 10/2001 |
| JP | 2009014702 A | 1/2009 |
| JP | 2014209081 A | 11/2014 |
| JP | 2016102747 A | 6/2016 |
| JP | 2017120257 A | 7/2017 |
| JP | 2018112566 A | 7/2018 |

OTHER PUBLICATIONS

JPO Notification of Reasons for Refusal for corresponding JP Application No. 2018-165314; dated Mar. 1, 2022.
GPO Office Action for corresponding DE Application No. 102019123153.1, dated Mar. 1, 2022.

* cited by examiner

*Primary Examiner* — Bach T Dinh
(74) *Attorney, Agent, or Firm* — Cantor Colburn LLP

(57) ABSTRACT

A nanopore device includes an aperture and an electrode pair. A transimpedance amplifier converts a current signal $I_S$ that flows through the nanopore device into a voltage signal $V_S$. The nanopore device measures small particles based on first data obtained by removing a DC component from the voltage signal $V_S$ and second data obtained based on the voltage signal $V_S$ from which the DC component has not been removed. Furthermore, the nanopore device is capable of monitoring the state of the nanopore device.

6 Claims, 8 Drawing Sheets

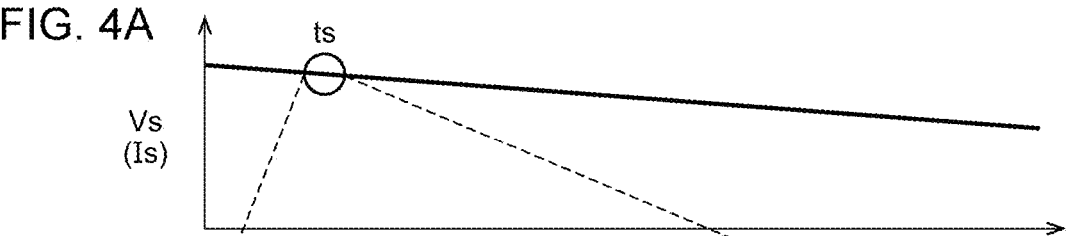
FIG. 4A
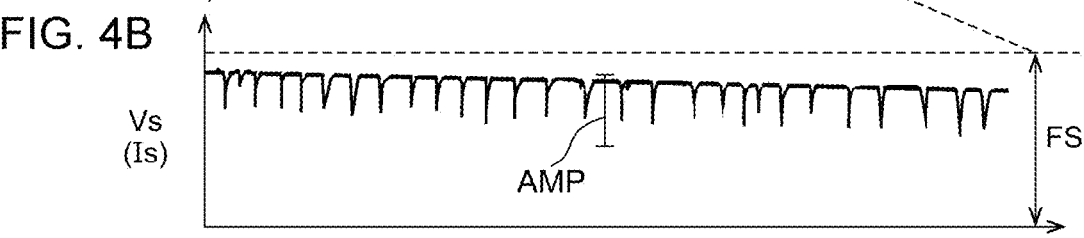
FIG. 4B
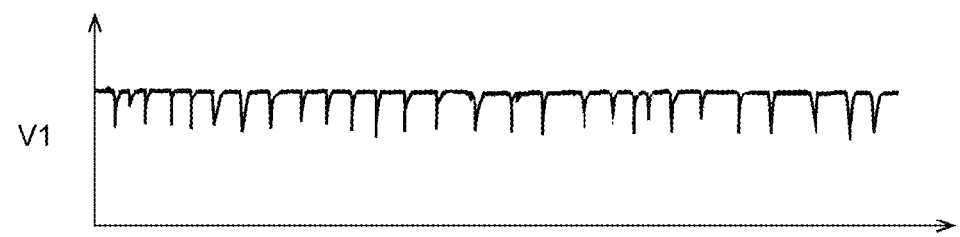
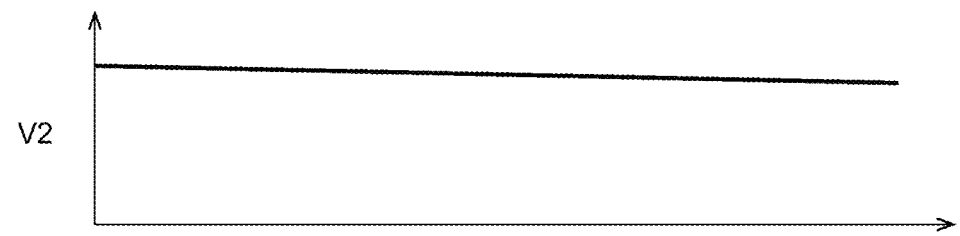

SMALL PARTICLE MEASUREMENT SYSTEM

CROSS-REFERENCE TO RELATED APPLICATION

The present application claims priority under 35 U.S.C. § 119 to Japanese Patent Application No. 2018-165314, filed on Sep. 4, 2018, the content of which are all incorporated herein by reference.

BACKGROUND OF THE INVENTION

1. Field of the Invention

The present invention relates to measurement employing a nanopore device.

2. Description of the Related Art

A particle size distribution measurement method, which is referred to as the "electrical sensing zone method (the Coulter principle)", is known. With this measurement method, an electrolyte solution including particles is applied such that it passes through an aperture that is referred to as a "nanopore". When a particle passes through such an aperture, the amount of the electrolyte solution with which the aperture is filled is reduced by an amount that corresponds to the volume of the particle, which raises the electrical resistance of the aperture. Accordingly, in a case in which the aperture has a thickness that is larger than the particle size, by measuring the electrical resistance of the aperture, this arrangement is capable of measuring the volume of the particle that passes through the aperture. Conversely, in a case in which the aperture has a thickness that is sufficiently smaller than the particle size, this arrangement is capable of measuring the cross-sectional area (i.e., particle diameter) of the particle that passes through the aperture.

FIG. 1 is a block diagram showing a small particle measurement system 1R employing the electrical sensing zone method. The small particle measurement system 1R includes a nanopore device 100, a measurement apparatus 200R, and a data processing apparatus 300.

The internal space of the nanopore device 100 is filled with an electrolyte solution 2 including particles 4 to be detected. The internal space of the nanopore device 100 is divided by a nanopore chip 102 so as to define two internal spaces. Electrodes 106 and 108 are provided to the two spaces. When an electric potential difference is generated across the electrodes 106 and 108, this generates a flow of ion current across the electrodes.

Furthermore, the particles 4 migrate by electrophoresis from a given space to the other space via the aperture 104.

The measurement apparatus 200R generates the electric potential difference between the electrode pair 106 and 108, and acquires information having a correlation with the resistance value Rp across the electrode pair. The measurement apparatus 200R includes a transimpedance amplifier 210, a voltage source 220, and a digitizer 230. The voltage source 220 generates an electric potential difference Vb between the electrode pair 106 and 108. The electric potential difference Vb functions as a driving source of the electrophoresis, and is used as a bias signal for measuring the resistance value Rp.

A small current Is flows through the electrode pair 106 and 108 in inverse proportion to the resistance of the aperture 104.

$$I_s = V_b / R_p \quad (1)$$

The transimpedance amplifier 210 converts the small current Is into a voltage signal Vs. With the conversion gain as r, the following expression holds true.

$$V_s = r \times I_s \quad (2)$$

By substituting Expression (1) into Expression (2), the following Expression (3) is obtained.

$$V_s = V_b \times r / R_p \quad (3)$$

The digitizer 230 converts the voltage signal Vs into digital data Ds. As described above, the measurement apparatus 200R is capable of acquiring the voltage signal Vs in inverse proportion to the resistance value Rp of the aperture 104.

FIG. 2 is a waveform diagram of an example of the small current Is measured by the measurement apparatus 200R. It should be noted that the vertical axis and the horizontal axis shown in the waveform diagrams and the time charts in the present specification are expanded or reduced as appropriate for ease of understanding. Also, each waveform shown in the drawing is simplified or exaggerated for emphasis or ease of understanding.

During a short period of time in which a particle passes through the aperture 104, the resistance value Rp of the aperture 104 becomes large. Accordingly, the current Is drops in the form of a pulse every time a particle passes through the aperture 104. The change in the current Is has a correlation with the particle size. The data processing apparatus 300 processes the digital data Ds so as to analyze the number of the particles 4 contained in the electrolyte solution 2, the particle distribution thereof, or the like.

RELATED ART DOCUMENTS

Patent Documents

Patent Document 1

Japanese Patent Application Laid Open No. 2009-014702

Patent Document 2

Japanese Patent Application Laid Open No. 2014-209081

Patent Document 3

Japanese Patent Application Laid Open No. 2017-120257

SUMMARY OF THE INVENTION

The present invention has been made in view of such a situation. Accordingly, it is an exemplary purpose of an embodiment of the present invention to provide a small particle measurement system that is capable of acquiring the state of a nanopore device in addition to acquiring the information with respect to particles.

An embodiment of the present invention relates to a small particle measurement system employing a nanopore device having an aperture and an electrode pair. The small particle measurement system comprises: a transimpedance amplifier structured to convert a current signal that flows through the nanopore device into a voltage signal; and a voltage source structured to apply a DC bias voltage between the electrode pair. The small particle measurement system is structured to measure small particles and to monitor a state of the nanopore device based on first data obtained by removing a DC component from the voltage signal and second data obtained based on the voltage signal without removing the DC component.

Another embodiment of the present invention relates to an information processing apparatus employed in a small particle measurement system. The small particle measurement system comprises: a nanopore device having an aperture and an electrode pair; and a measurement apparatus structured to apply a voltage between the electrode pair, to detect a current that flows through the electrode pair, and to generate first data, of which a DC component has been removed, and second data, which includes a DC component. The information processing apparatus comprises a processor configured to execute processing for detecting a small particle based on the first data and to execute processing for monitoring a state of the nanopore device based on the second data.

Yet another embodiment of the present invention relates to a measurement method for measuring a small particle. The measurement method comprises: filling a nanopore device having an aperture and an electrode pair with an electrolyte solution containing small particles; applying a voltage between the electrode pair, and measuring a current waveform that flows through the electrode pair; generating first data obtained by removing a DC component from the current waveform, and generating second data including a DC component; detecting a small particle based on the first data; and monitoring a state of the nanopore device based on the second data.

Yet another embodiment of the present invention relates to a measurement apparatus structured to measure a nanopore device having an aperture and an electrode pair. The measurement apparatus comprises: a transimpedance amplifier structured to convert a current signal that flows through the nanopore device into a voltage signal; a voltage source structured to apply a DC bias voltage between the electrode pair; a high-pass filter structured to remove a DC component from the voltage signal; a first A/D converter structured to convert an output of the high-pass filter into first data; a second A/D converter structured to convert the voltage signal before it passes through the high-pass filter into second data; a first cache group structured to store the first data; a second cache group structured to store the second data; a cache controller structured to write the first data and the second data to the first cache group and the second cache group, and to read out the first data and the second data; and a bus controller structured to transmit the first data and the second data read out by the cache controller to an external information processing apparatus.

It is to be noted that any arbitrary combination or rearrangement of the above-described structural components and so forth is effective as and encompassed by the present embodiments. Moreover, this summary of the invention does not necessarily describe all necessary features so that the invention may also be a sub-combination of these described features.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 4A and FIG. 4B are waveform diagrams showing the waveforms of a voltage signal, a first signal, and a second signal;

DETAILED DESCRIPTION OF THE INVENTION

The invention will now be described based on preferred embodiments which do not intend to limit the scope of the present invention but exemplify the invention. All of the features and the combinations thereof described in the embodiment are not necessarily essential to the invention.

In the present specification, the state represented by the phrase "the member A is coupled to the member B" includes a state in which the member A is indirectly coupled to the member B via another member that does not substantially affect the electric connection between them, or that does not damage the functions or effects of the connection between them, in addition to a state in which they are physically and directly coupled.

Similarly, the state represented by the phrase "the member C is provided between the member A and the member B" includes a state in which the member A is indirectly coupled to the member C, or the member B is indirectly coupled to the member C via another member that does not substantially affect the electric connection between them, or that does not damage the functions or effects of the connection between them, in addition to a state in which they are directly coupled.

Basic Configuration

Figure 3:
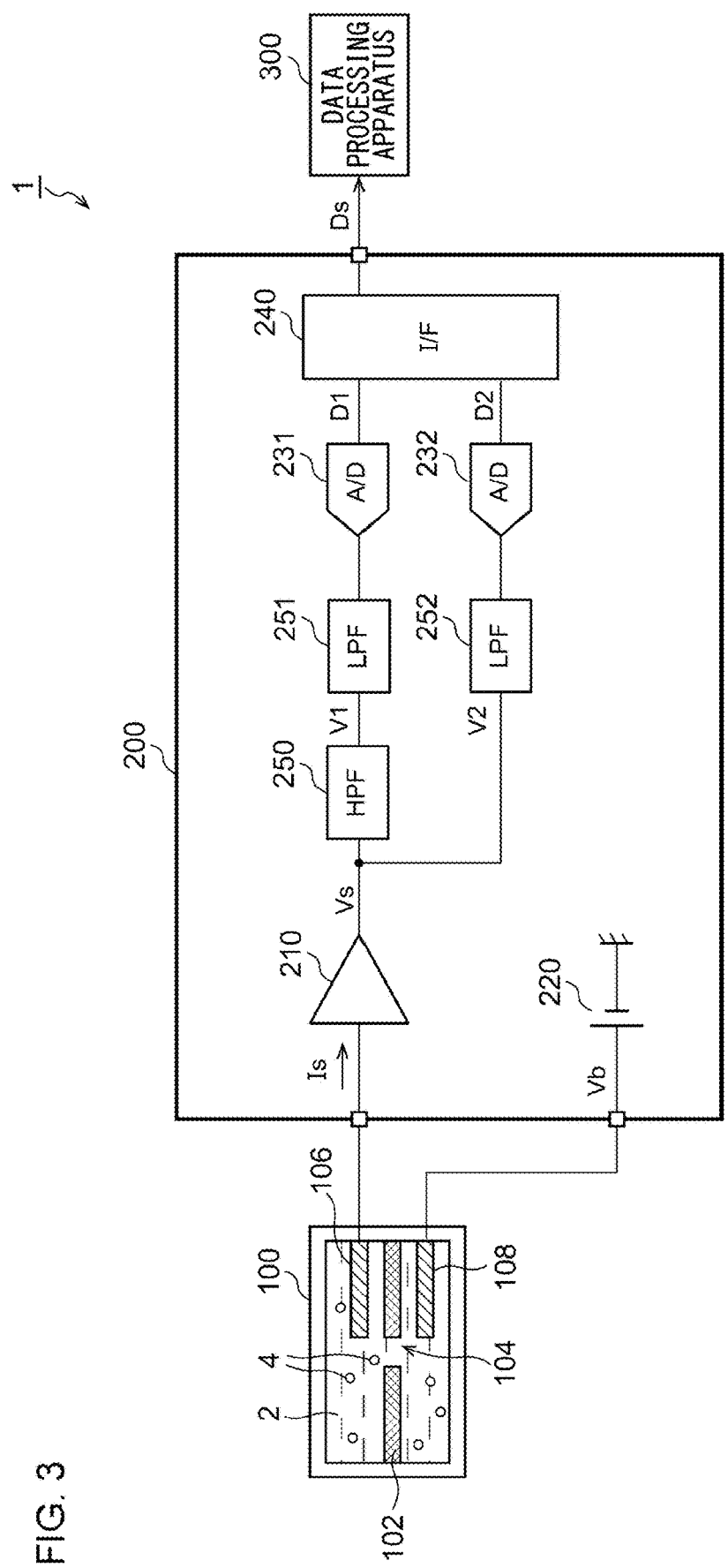
FIG. 3 is a block diagram showing a small particle measurement system according to an embodiment.

FIG. 3 is a block diagram showing a small particle measurement system 1 according to an embodiment. The small particle measurement system 1 includes a nanopore device 100, a measurement apparatus 200, and a data processing apparatus 300.

Figure 1:
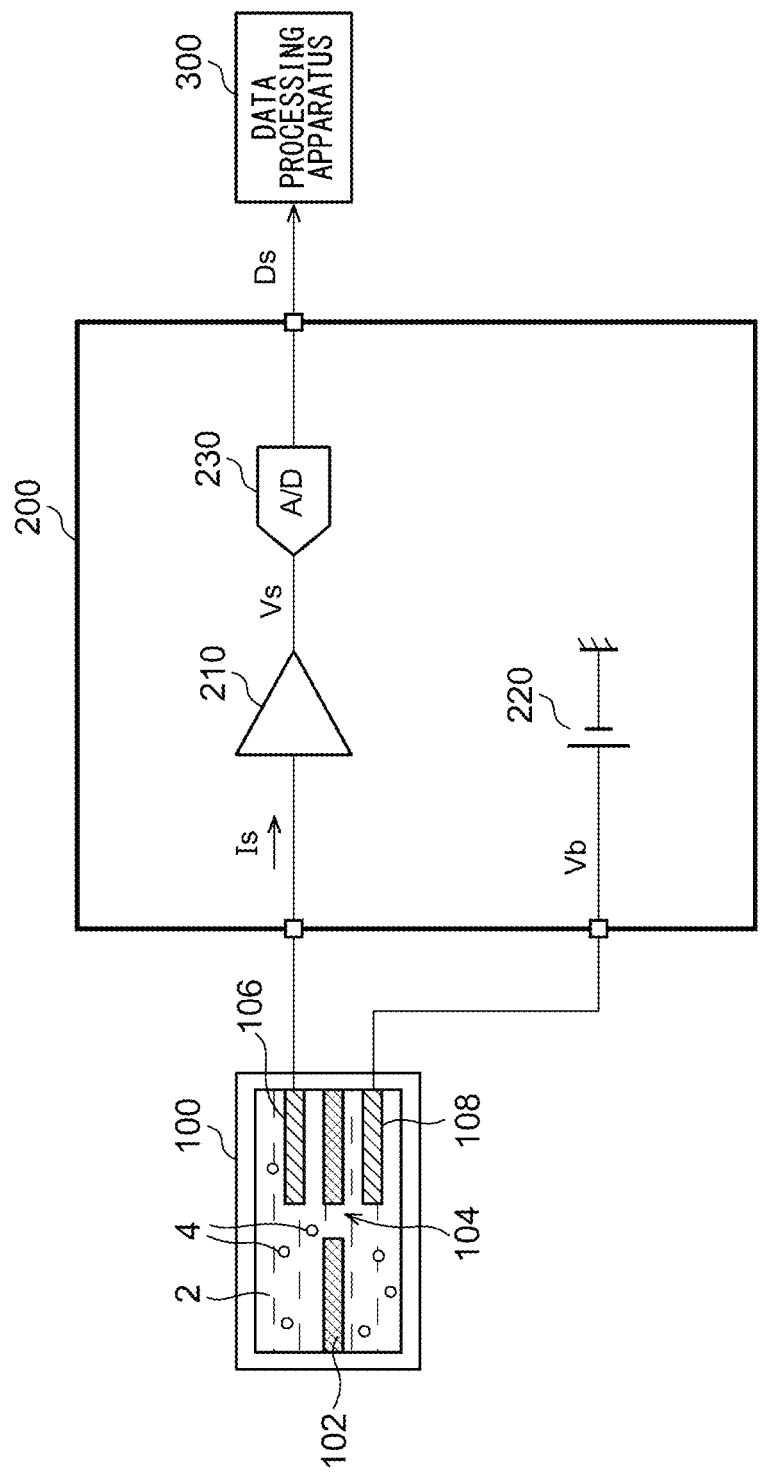
FIG. 1 is a block diagram showing a small particle measurement system employing an electrical sensing zone method.
Figure 2:
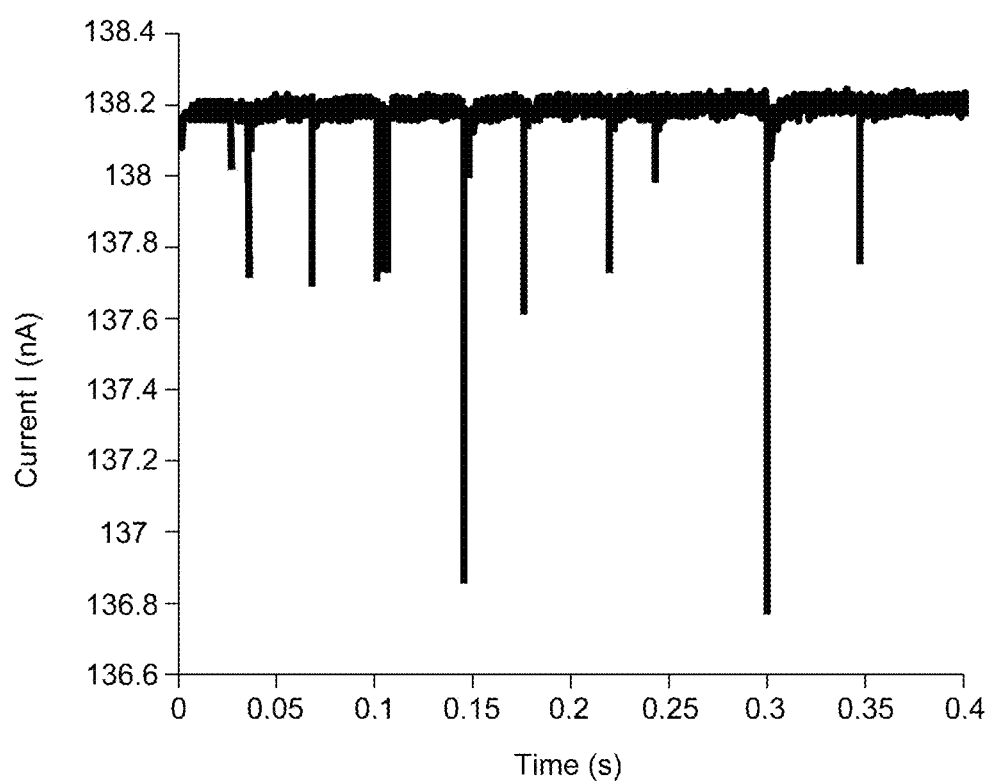
FIG. 2 is a waveform diagram showing an example of a small current $I_S$ measured by a measurement apparatus.

As described with reference to FIG. 1, the nanopore device 100 includes a nanopore chip 102 provided with an aperture 104 and an electrode pair 106 and 108. An internal space of the nanopore chip 102 is filled with an electrolyte solution such as a KCl (potassium chloride) solution, PBS (phosphate buffered saline) solution, or the like.

The measurement apparatus 200 is structured to force a voltage between the electrode pair 106 and 108, and of measuring a current $I_S$ that flows through the aperture 104. The measurement apparatus 200 includes a transimpedance amplifier 210 and a voltage source 220 as a front-end circuit. The voltage source 220 applies a DC bias voltage Vb between the electrode pair 106 and 108. The transimpedance amplifier 210 converts the current $I_S$ that flows through the nanopore device 100 into a voltage signal $V_S$.

The small particle measurement system 1 is capable of measuring the particles 4 contained in the electrolyte solution 2 based on first data D1 obtained by removing a DC component from the voltage signal $V_S$ and second data D2 obtained without removing the DC component from the voltage signal $V_S$. Furthermore, the small particle measurement system 1 is capable of monitoring the state of the nanopore device 100 (or the state of nanopore chip 102).

In order to acquire the first data D1 and the second data D2, the measurement apparatus 200 includes a high-pass filter 250, a first A/D converter 231, and a second A/D converter 232. The high-pass filter 250 removes a DC component (baseline component) from the voltage signal $V_S$. The first data D1 is generated based on the output V1 of the high-pass filter 250. On the other hand, the second data D2 is generated based on the voltage signal $V_S$ received without involving the high-pass filter 250.

The first A/D converter 231 converts a first signal V1, which is an output signal of the high-pass filter 250, into the first data D1 in the form of digital data. As an upstream stage of the first A/D converter 231, an anti-aliasing filter 251 is inserted.

The input signal $V_S$ of the high-pass filter 250 is input as the second signal V2 to the second A/D converter 232. An anti-aliasing filter 252 may be inserted as an upstream stage of the second A/D converter 232. After the second signal V2 passes through the anti-aliasing filter 252, unnecessary high-frequency components are removed from the second signal V2, and the DC component of the voltage signal $V_S$ remains in the second signal V2. The first A/D converter 231 and the second A/D converter 232 may be designed to have different resolutions and different sampling rates.

The interface 240 transmits the first data D1 and the second data D2 to the data processing apparatus 300, and receives a control signal from the data processing apparatus 300.

The data processing apparatus 300 functions as an interface with the user. Furthermore, the data processing apparatus 300 integrally controls the small particle measurement system 1, and has functions of acquiring, storing, and displaying measurement results. The data processing apparatus 300 may be configured as a general-purpose computer or a workstation. Also, the data processing apparatus 300 may be configured as a dedicated hardware component designed for the small particle measurement system 1.

The data processing apparatus 300 processes the first data D1 and the second data D2 received from the measurement apparatus 200 so as to acquire the number of particles 4 contained in the electrolyte solution 2 and the particle sizes thereof, and to monitor the state of the nanopore device 100.

For example, the data processing apparatus 300 is configured as an information processing apparatus such as a laptop computer, desktop computer, tablet terminal, or the like. The functions of the data processing apparatus 300 described in the present specification are supported by a processor (CPU: Central Processing Unit) included in the information processing apparatus and a software program to be executed by the processor.

The above is the configuration of the small particle measurement system 1. Next, description will be made regarding the operation thereof. FIG. 4A and FIG. 4B are waveform diagrams showing the voltage signal $V_S$, the first signal V1, and the second signal V2. The vertical axis and the horizontal axis shown in the waveform diagrams and the time charts used as references in the present specification are expanded or reduced as appropriate for ease of understanding. Also, each of the waveforms shown in the drawings are simplified or exaggerated for emphasis or ease of understanding.

FIG. 4A shows a waveform of the baseline of the voltage signal $V_S$ (current signal $I_S$) from a macro viewpoint on a long time scale. From the viewpoint of such a long time scale, the baseline of the voltage signal $V_S$ decreases with time. In other words, from the viewpoint of such a long time scale, the impedance of the nanopore device 100 rises with time. Known reasons why the impedance rises with time include the formation of an oxide film on the electrode surface, adhesion of contamination, and the like.

FIG. 4B shows an enlarged waveform of FIG. 4A on a short time scale ts. The voltage signal $V_S$ is observed as a waveform having spike-like signal components, each of which corresponds to the passage of a particle, superimposed on the baseline component. The first signal V1 has a waveform that corresponds to the signal components. The second signal V2 has a waveform that corresponds to the baseline. That is to say, the first data D1 acquired from the first signal V1 represents the signal components. The second data D2 acquired from the second signal V2 represents the baseline component.

The small particle measurement system 1 is capable of measuring the diameter of each particle based on the first data D1. Furthermore, the small particle measurement system 1 is capable of monitoring the state of the nanopore device 100. Examples of the state of the nanopore device 100 include clogging of the aperture 104.

Figure 5:
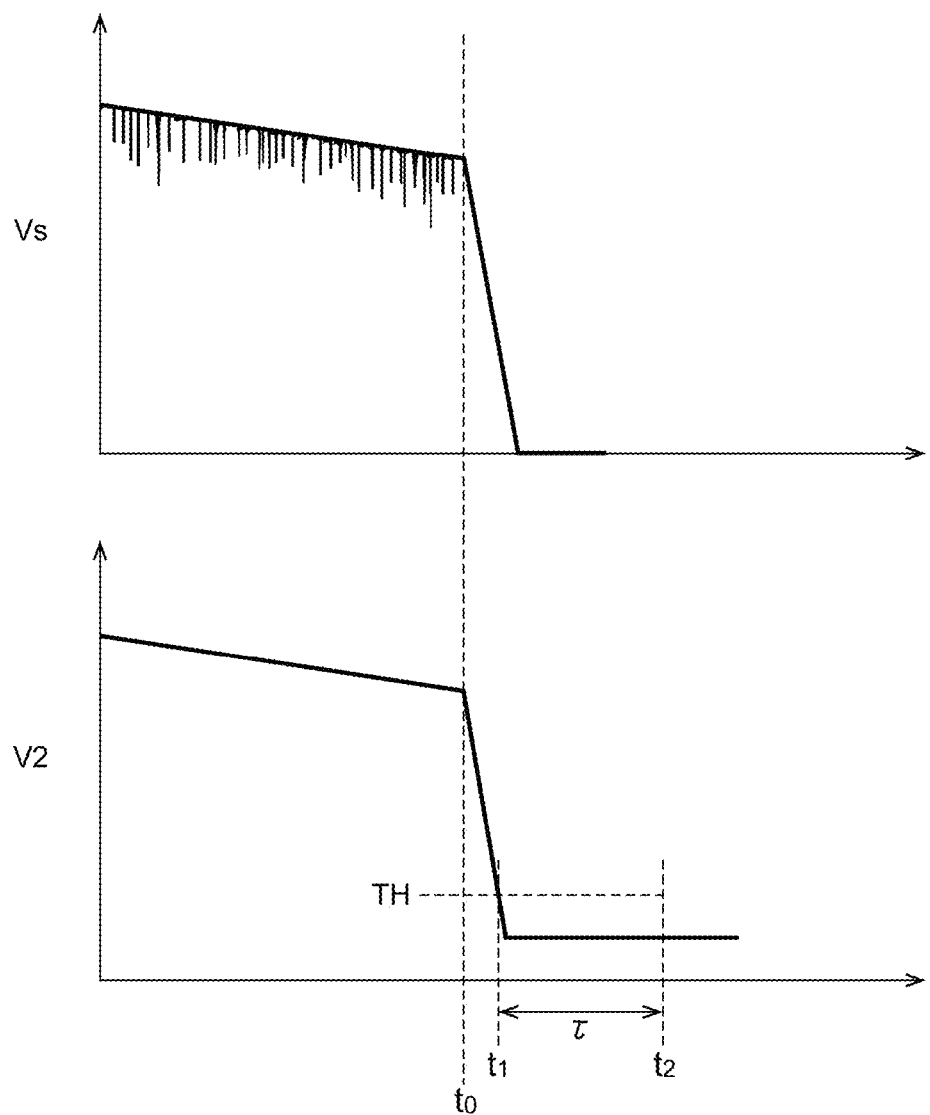
FIG. 5 is a diagram for explaining detection of clogging of an aperture.

FIG. 5 is a diagram for explaining detection of clogging of the aperture 104. Before the time point $t_0$, no clogging occurs. There is only a gradual change in the baseline of the voltage signal $V_S$. Accordingly, there is only a gradual change in the second signal V2. When the aperture 104 is clogged with particles or other debris, this raises the impedance across the electrodes, i.e., this impairs the flow of the current signal $I_S$, which lowers the baseline of the voltage signal $V_S$. For example, when the second data D2 satisfies a predetermined condition, the data processing apparatus 300 judges that a clogging abnormality has occurred, and is capable of issuing a notification or warning to the user. As such a predetermined condition, when the second data D2 remains smaller than a predetermined value over a predetermined period of time, the data processing apparatus 300 may judge that a clogging abnormality has occurred. In the example shown in FIG. 5, the second data D2 becomes smaller than a predetermined threshold value $T_H$ at the time point $t_1$. At the time point $t_2$ after a predetermined period of time τ elapses, judgement is made that a clogging abnormality has occurred.

It should be noted that the state of the nanopore device 100 to be monitored by the small particle measurement system 1 is not restricted to such clogging of the aperture 104. Rather, examples of such a state include various kinds of phenomena and states having a correspondence with the baseline. For example, the baseline depends on the concentration of the electrolyte solution 2 with which the nanopore device 100 is filled. The electrolyte solution 2 is prepared by the user using a regent, which involves variation in the concentration. Accordingly, the small particle measurement system 1 is capable of monitoring the concentration of the electrolyte solution 2, or of detecting an abnormality that can occur in the concentration.

The baseline changes according to the distance between the electrode pair 106 and 108. The nanopore device 100 is manufactured with a semiconductor process. Accordingly, the distance between the electrode pair 106 and 108 is affected by process variation. Furthermore, the diameter of the aperture 104 and the thickness of the nanopore chip 102 each have an effect on the baseline. Accordingly, the small particle measurement system 1 is capable of detecting a manufacturing fault in the nanopore device 100 and a temporary abnormality.

Furthermore, the small particle measurement system 1 has the following advantage. With the full scale of the voltage signal $V_S$ as FS, the maximum value $A_{MAX}$ of the amplitude of the signal component is relatively smaller than the full scale FS. In a case in which the voltage signal $V_S$ is input to the A/D converter, the input dynamic range of the A/D converter is required to be determined giving consideration to the full scale FS. Such an arrangement involves poor resolution of the signal component. For example, in a case in which the A/D converter has a 10-bit resolution and the maximum value $A_{MAX}$ of the amplitude is ¼ the full scale FS, such an arrangement supports only an 8-bit resolution for the signal component.

The measurement apparatus 200 shown in FIG. 3 is configured to generate a first signal V1 having no baseline, and to instruct the first A/D converter 231 to acquire the first signal V1. Accordingly, the input dynamic range of the first A/D converter 231 can be designed based on the maximum value $A_{MAX}$ of the amplitude (full scale of the first signal V1) instead of the full scale of the voltage signal $V_S$. This allows the signal component to be acquired with high resolution.

The first A/D converter 231 receives, as an input signal, a signal component that changes at a high speed. In contrast, the second A/D converter 232 receives, as an input signal, the baseline, which gradually changes. Accordingly, the first A/D converter 231 may preferably be designed to have a relatively higher sampling rate than that of the second A/D converter 232.

Furthermore, the first A/D converter 231 receives, as an input signal, a signal component that changes in a small range. In contrast, the second A/D converter 232 receives, as an input signal, the baseline, which changes in a wide range. Accordingly, the first A/D converter 231 may preferably be designed to have a higher resolution than that of the second A/D converter 232.

Figure 6:
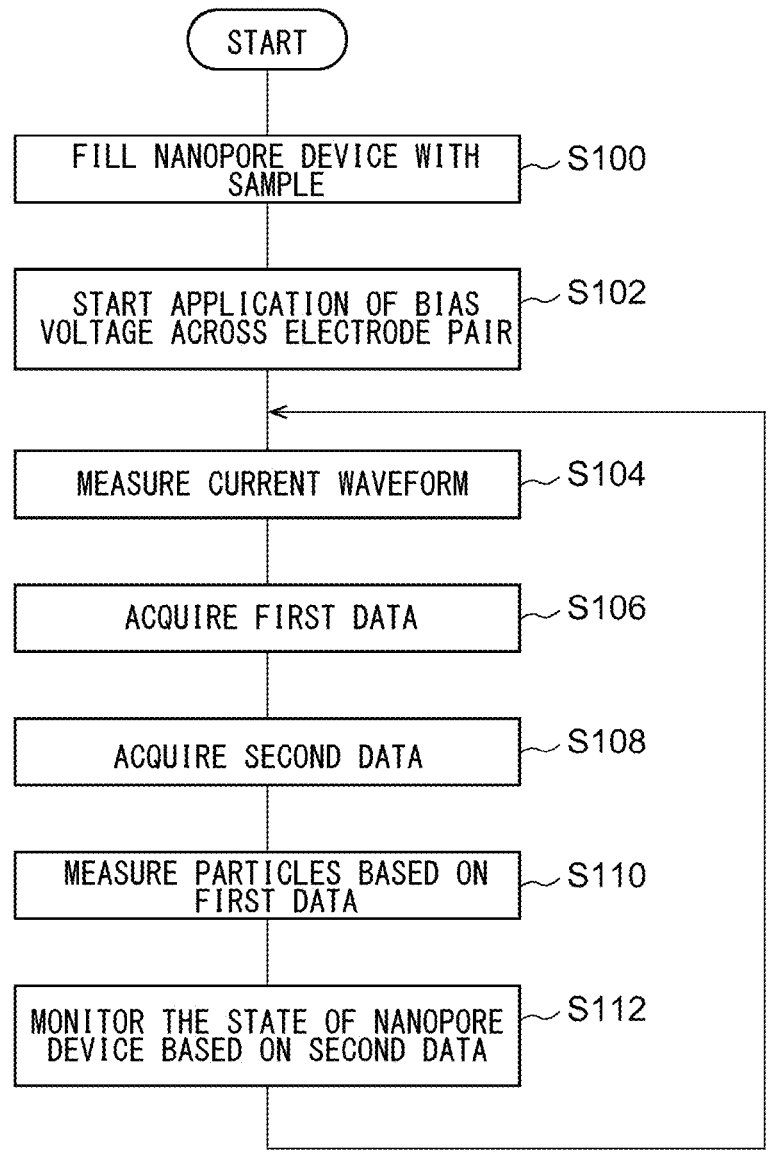
FIG. 6 is a flowchart of small particle measurement supported by a small particle measurement system.

FIG. 6 is a flowchart showing small particle measurement supported by the small particle measurement system 1. First, the nanopore device 100 including the aperture 104 and the electrode pair 106 and 108 is filled with the electrolyte solution 2 containing the particles 4 (S100). Subsequently, the measurement apparatus 200 starts to apply the bias voltage Vb between the electrode pair 106 and 108 (S102). Subsequently, the current waveform that flows through the electrode pair 106 and 108 is measured (S104). The first data D1 including no DC component of the current waveform and the second data D2 including such a DC component are generated at respective sampling rates (S106 and S108). The data processing apparatus 300 detects particles based on the first data D1 (S110), and detects the state of the nanopore device 100 based on the second data D2 (S112).

It should be noted that the processing and the order of the steps shown in the flowchart can be modified as long as such a modification involves no problem in the processing. Also, processing related to the first data D1 and the second data D2 may be executed in parallel simultaneously.

Figure 7:
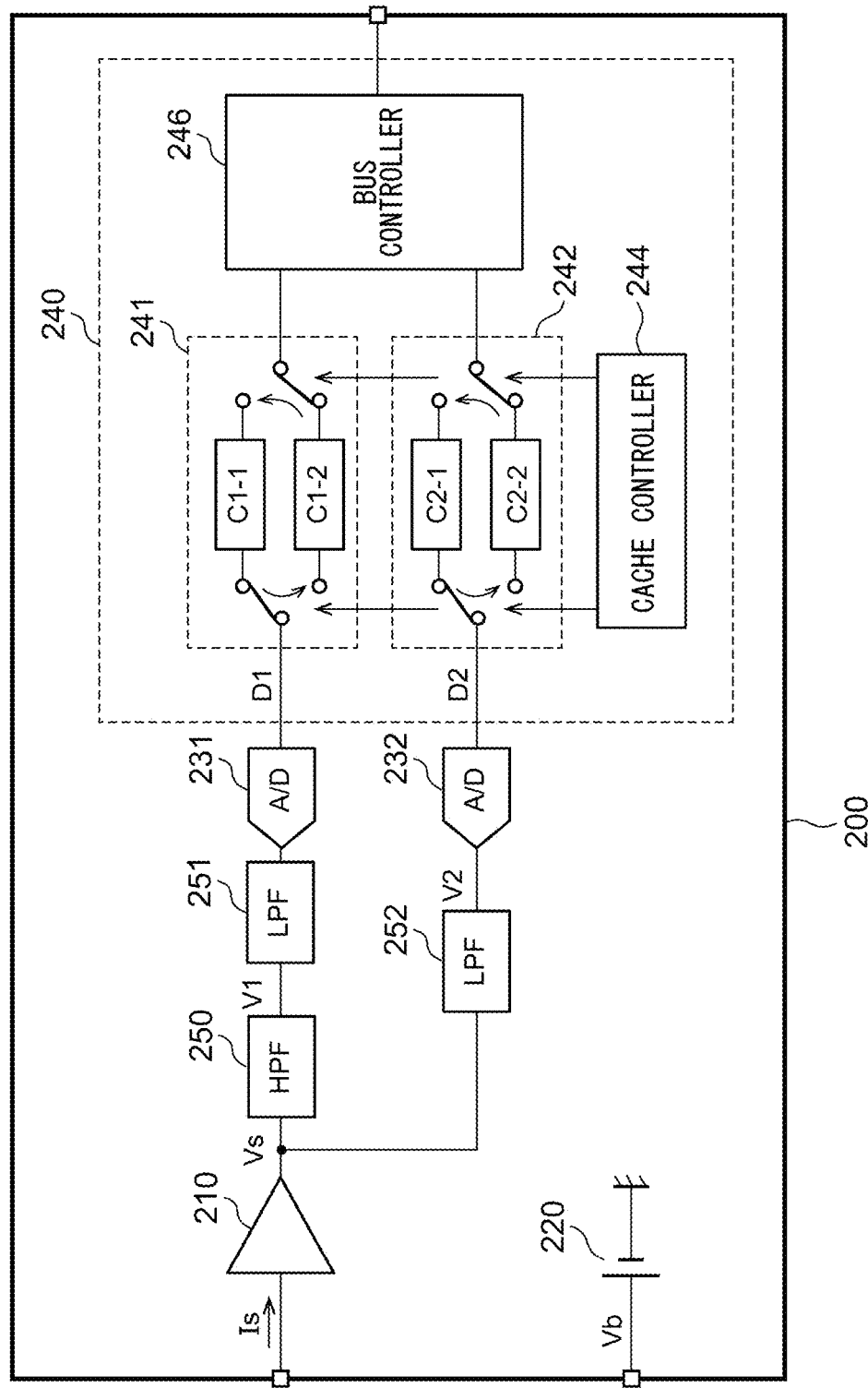
FIG. 7 is a block diagram showing a measurement apparatus.

Next, description will be made regarding a specific example configuration of the nanopore device 100. FIG. 7 is a block diagram showing the measurement apparatus 200.

The interface 240 includes a first cache group 241, a second cache group 242, a cache controller 244, and a bus controller 246. The first cache group 241 includes multiple (two in this example) caches C1-1 and C1-2, and stores the first data D1. The second cache group 242 includes multiple caches C2-1 and C2-2, and stores the second data D2.

The cache controller 244 includes: a write controller configured to control the writing of the first data D1 to the first cache group 241 and to control the writing of the second data D2 to the second cache group 242; and a read controller configured to control the reading of the first data D1 from the first cache group 241, and to control the reading of the second data D2 from the second cache group 242.

Specifically, the write controller selects, as a write target, one from among the multiple caches C1-1 and C1-2 included in the first cache group 241, and sequentially writes the first data D1 to the cache thus selected. On the other hand, the read controller selects, as a read target, one from among the caches included in the first cache group 241 except for the cache selected as the write target by the write controller, and reads out the first data D1 from the cache thus selected. The same can be said of the second cache group 242 side.

The bus controller 246 transmits the first data D1 and the second data D2 thus read out by the cache controller 244 to an external information processing apparatus (data processing apparatus 300 shown in FIG. 3).

As described above, the sampling rate of the first A/D converter 231 is higher than that of the second A/D converter 232. Furthermore, the first A/D converter 231 is configured as a higher-bit A/D converter than the second A/D converter 232.

When a full-cache event has occurred in either the first cache group 241 or the second cache group 242, the cache controller 244 switches the write-target caches, and switches each cache selected in the previous step as the write-target cache to the read-target cache. Subsequently, the cache controller 244 starts to read the first data D1 and the second data D2.

Figure 8:
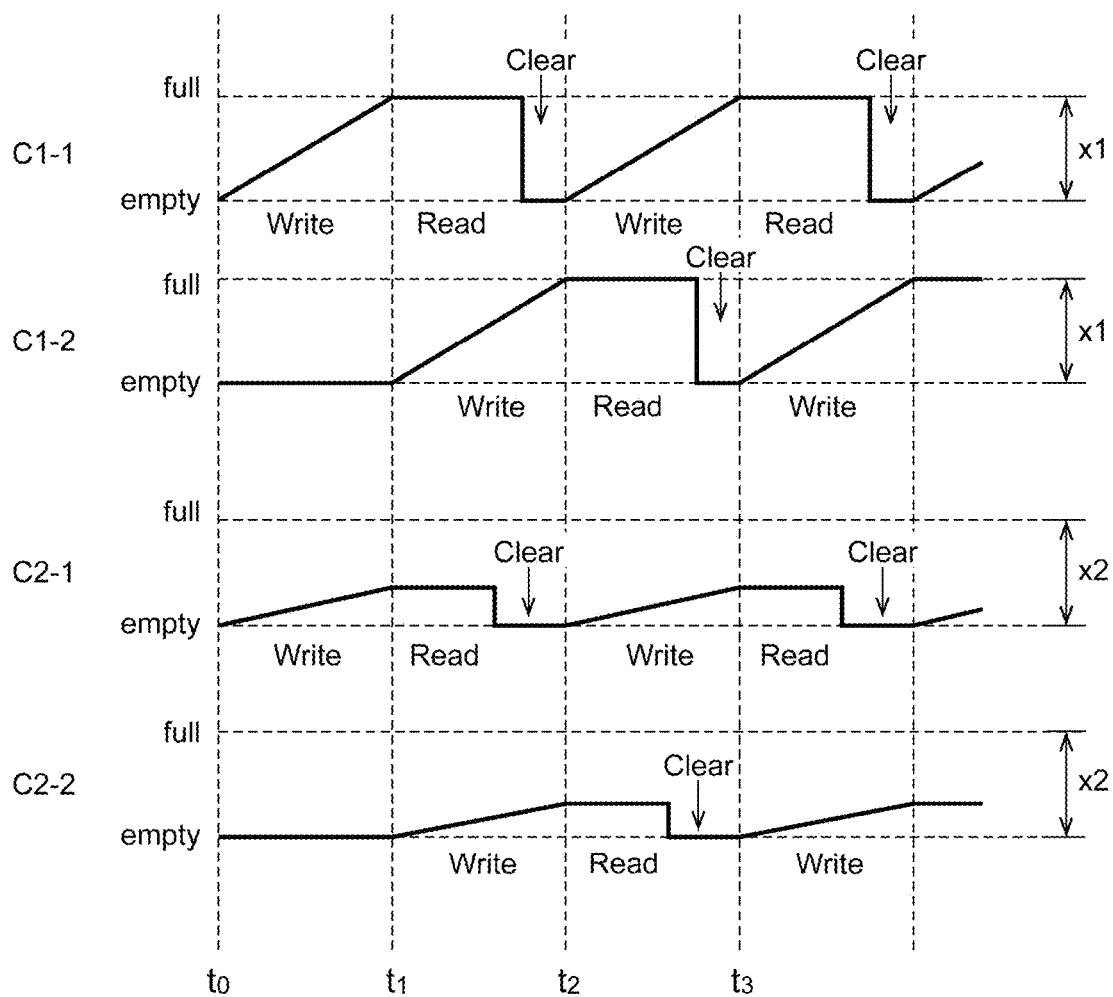
FIG. 8 is a diagram for explaining a cache control operation of the measurement apparatus shown in FIG. 7.

FIG. 8 is a diagram for explaining a cache control operation of the measurement apparatus 200 shown in FIG. 7. FIG. 8 shows the amount of data stored in each cache.

At the time point to, the data processing apparatus 300 transmits a measurement start instruction to the measurement apparatus 200. In response to the measurement start instruction, the cache controller 244 starts a control operation for the first A/D converter 231 and the second A/D converter 232, and a write control operation for the first cache group 241 and the second cache group 242.

First, the caches C1-1 and C2-1 are selected as the write-target caches. The first data D1 and the second data D2 are written to the caches C1-1 and C2-1 thus selected, respectively.

For ease of understanding, description will be made regarding an example in which the number of bits that form the first data D1 (e.g., 14 bits) is smaller than one word (e.g., 16 bits) supported by each cache C1 included in the first cache group 241. In the same manner, the number of bits that form the second data D2 (e.g., 10 bits) is smaller than one word (e.g., 16 bits) supported by each cache C2 included in the second cache group 242.

Description will be made with the number of words supported by each cache C1 as X1, and with the number of words supported by each cache C2 as X2. Furthermore, description will be made with the sampling rate of the A/D converter 231 as r1, and with the sampling rate of the second A/D converter 232 as r2. The times of periods T1 and T2 that elapse before the respective caches C1 and C2 become full are represented by the following Expressions.

$$T1 = X1/r1$$

$$T2 = X2/r2$$

Description will be made below assuming that the relation T1<T2 holds true. Here, r1 and r2 each correspond to the slope of an increase of the amount of data stored in the corresponding cache.

At the time point $t_1$ (=T1), the cache C1-1 on the first cache group 241 side becomes full. In response to this full-cache event as a trigger, the cache controller 244 switches the caches C1-1 and C2-1, which had been set to the write-target caches, to the read-target caches. Subsequently, the cache controller 244 reads out the first data D1 and the second data D2 respectively stored in the caches C1-1 and C2-1 thus selected as the read-target caches, and transmits the first data D1 and the second data D2 to the data processing apparatus 300. After the data reading operation is completed, the data stored in the corresponding cache may be cleared.

After the time point $t_1$, the caches C1-2 and C2-2 are selected as the write-target caches. The first data D1 and the second data D2 are written to the caches C1-2 and C2-2 thus selected. Subsequently, when the cache C1-2 on the first cache group 241 side becomes full at the time point $t_2$, the read-target caches and the write-target caches are switched again. Subsequently, the same operation is repeated.

Description will be made assuming that the sum total of the number of bits (16 bits) that form one word supported by the cache C1 and the number of bits (16 bits) that form one word supported by the cache C2 is equal to or smaller than the data width of the bus. In this case, such an arrangement allows the first data D1 and the second data D2 to be read out in increments of one word, and to be output to the bus at the same time. The number of read operations may preferably be determined based on data configured of a larger number of words. In this example, the number of words X1 that form the first data D1 is determined as the number of read operations. Each cache C2 stores the second data D2 configured of (r2×T1) words. Accordingly, the (r2×T1+1)-th word and subsequent words may preferably be invalidated.

The advantages of the cache control operation described above can be clearly understood in comparison with a comparison technique. With such a comparison technique, when a full-cache event has occurred in the first cache group 241, a read instruction is issued for the first cache group 241. On the other hand, when a full-cache event has occurred in the second cache group 242, a read instruction is issued for the second cache group 242. The full-cache event occurs in the first cache group 241 and the second cache group 242 in an asynchronous manner. Such an arrangement involves the occurrence of a situation in which the read instruction for the first cache group 241 and the read instruction for the second cache group 242 are issued at the same time (which will be referred to as a "collision"). In this case, after the read operation is completed for one from among the first cache group 241 and the second cache group 242, the read operation for the other cache group is started, leading to a problem of a long period of time required to read the data. Furthermore, in some cases, depending on a situation, the read instruction for one from among the caches is not appropriately received, leading to a problem of missing data.

In contrast, the measurement apparatus 200 shown in FIG. 7 does not involve such a collision in which two read instructions are issued at the same time. This allows the first data D1 and the second data D2 to be transmitted to the data processing apparatus 300 in a sure manner.

With the comparison technique, in a case in which two read instructions are issued at different timings, the bus is occupied for the sum total of the time required to read data from the cache C1 and the time required to read data from the cache C2. In contrast, with the measurement apparatus 200 shown in FIG. 7, data can be read from the cache C1, which is one from among two kinds of caches, during a period of time for which data is read from the cache C1, which is the other kind of cache. This allows the bus occupation time to be reduced.

Furthermore, with the comparison technique, from among the data width of the bus (32-bit), only 16-bit data is transmitted in each of the first data D1 transmission and the second data D2 transmission, and accordingly, waste occurs. In contrast, the measurement apparatus 200 shown in FIG. 7 is capable of effectively exploiting the data width of the bus.

Description has been made above regarding the present invention with reference to the embodiment. The above-described embodiment has been described for exemplary purposes only, and is by no means intended to be interpreted restrictively. Rather, it can be readily conceived by those skilled in this art that various modifications may be made by making various combinations of the above-described components or processes, which are also encompassed in the technical scope of the present invention. Description will be made below regarding such modifications.

First Modification

Description has been made in the embodiment regarding an arrangement in which the first signal V1 and the second signal V2 are each generated in the analog domain so as to acquire the digital data D1 and D2. However, the present invention is not restricted to such an arrangement. For example, the voltage signal $V_S$ may be converted into a digital signal $D_S$ by means of a high-speed, high-resolution A/D converter. Also, the first data D1 and the second data D2 may be generated by digital signal processing. Specifically, the digital signal $D_S$ may be processed by a digital high-pass filter so as to generate the first data D1. Also, the digital data $D_S$ may be processed by a digital low-pass filter so as to generate the second data D2.

For example, the measurement apparatus 200 may transmit the digital signal $D_S$ to the data processing apparatus 300. Also, the data processing apparatus 300 may generate the first data D1 and the second data D2 by data processing.

Also, the measurement apparatus 200 may mount a digital filter or otherwise a processor configured to generate the first data D1 and the second data D2 based on the digital signal $D_S$. Also, the measurement apparatus 200 may transmit the first data D1 and the second data D2 thus generated to the data processing apparatus 300.

Second Modification

Description has been made in the embodiment regarding an arrangement in which the second data D2 is generated using a low-pass filter (anti-aliasing filter). However, the present invention is not restricted to such an arrangement. Also, such a low-pass filter may be omitted. This is because the second data D2 is only required to provide information that can be used to monitor the state of the nanopore device, i.e., to allow only a rough current level to be acquired. Accordingly, even in a case in which the second data D2 has sampling noise or the like, this does not have a large effect.

Third Modification

The first data D1 and the second data D2 may be transmitted from the measurement apparatus 200 to the data processing apparatus 300 in the following manner. For example, in a case in which the number of bits that form the first data D1 and the number of bits that form the second data D2 are each larger than the data width of the bus, as a first step, all the first data D1 may be read out from the first cache group 241, and may be transmitted to the data processing apparatus 300. Subsequently, as a second step, all the second data D2 may be read out from the second cache group 242, and may be transmitted to the data processing apparatus 300.

Fourth Modification

The measurement apparatus 200 shown in FIG. 7 may employ a dual-port cache that is capable of simultaneously reading and writing data for the same address.

Fifth Modification

Description has been made in the present specification regarding a small particle measurement apparatus. However, the present invention is not restricted to such an application. Also, the present invention is widely applicable to various kinds of measurement devices that support microcurrent measurement using a nanopore device, examples of which include DNA sequencers.

While the preferred embodiments of the present invention have been described using specific terms, such description is for illustrative purposes only, and it is to be understood that changes and variations may be made without departing from the spirit or scope of the appended claims.

What is claimed is:

1. A small particle measurement system employing a nanopore device having an aperture and an electrode pair, the small particle measurement system comprising:
a transimpedance amplifier structured to convert a current signal that flows through the nanopore device into a voltage signal; and
a voltage source structured to apply a DC bias voltage between the electrode pair,
and wherein the small particle measurement system is structured to measure small particles and to monitor a state of the nanopore device based on first data obtained by removing a DC component from the voltage signal and second data obtained based on the voltage signal without removing the DC component.

2. The small particle measurement system according to claim 1, structured to be capable of detecting clogging in the nanopore device.

3. The small particle measurement system according to claim 1, further comprising a high-pass filter structured to receive the voltage signal,
wherein the first data is based on an output of the high-pass filter,
and wherein the second data is based on a signal that has not passed through the high-pass filter.

4. The small particle measurement system according to claim 3, further comprising:
a first A/D converter structured to convert an output of the high-pass filter into first digital data; and
a second A/D converter structured to convert a signal that has not passed through the high-pass filter into second digital data.

5. The small particle measurement system according to claim 4, wherein the first A/D converter is structured to have a resolution that is higher than that of the second A/D converter.

6. The small particle measurement system according to claim 4, wherein the first A/D converter is structured to have a sampling rate that is higher than that of the second A/D converter.

* * * * *